United States Patent [19]

Markofsky

[11] 4,424,385
[45] Jan. 3, 1984

[54] SYNTHESIS OF NITROMETHANE

[75] Inventor: Sheldon B. Markofsky, 19340 Olney Mill Rd., Olney, Md. 20832

[73] Assignee: W. R. Grace & Co., New York, N.Y.

[21] Appl. No.: 404,127

[22] Filed: Aug. 2, 1982

[51] Int. Cl.$^3$ ............................................. C07C 76/02
[52] U.S. Cl. .................................................. 568/948
[58] Field of Search ................................. 568/947, 948

[56] References Cited

FOREIGN PATENT DOCUMENTS

| | | | |
|---|---|---|---|
| 54-125604 | 9/1979 | Japan | .................................. 568/948 |
| 56-169648 | 12/1981 | Japan . | |
| 56-169649 | 12/1981 | Japan . | |
| 918291 | 9/1982 | U.S.S.R. . | |

*Primary Examiner*—Leland A. Sebastian
*Attorney, Agent, or Firm*—Howard J. Troffkin

[57] ABSTRACT

An improved process for forming nitromethane by contacting liquid methyl halide with an alkali or alkaline earth metal nitrite in the presence of an excess of the liquid methyl halide.

7 Claims, No Drawings

SYNTHESIS OF NITROMETHANE

BACKGROUND OF THE INVENTION

The present invention is directed to a process of producing nitroparaffin, in particular nitromethane, by nitration of liquid methyl halide with an alkali or alkaline earth metal nitrite in an excess of the liquid methyl halide. The present process has unexpectedly been found to produce nitromethane in high yields and at more rapid rates of reaction without the need for the use of an aprotic solvent and the problems associated therewith.

Nitromethane is a highly desired product which has many uses. It is a known preservative for chlorinated hydrocarbons, a fuel additive and an intermediate compound in the formation of various other chemicals, such as chlorpicrin. Nitromethane is the most commercially desired compound of the nitroparaffins.

Homogeneous gas phase nitration of hydrocarbon feed is presently commercially used to form nitroparaffins. This process, as described in U.S. Pat. Nos. 3,780,115; 3,869,253; and 4,260,838 as well as French Publication 70/32118 requires the contacting of a gaseous feed of saturated hydrocarbons higher than methane with nitrogen peroxide in the presence of oxygen under elevated temperature and pressure. A mixture of nitroparaffins is produced with the nitromethane component being in low yields.

Preparation of nitroparaffins from alkyl halide and excess alkali metal nitrite has been proposed. The reaction is taught to be required to be carried out in an aprotic polar solvent such as dimethyl formamide, dimethyl sulfoxide, N-methyl pyrrolidone, and hexamethyl phosphoramide. Further, such processes may be catalyzed by phase transfer agents such as crown ethers (e.g. 18-crown-6, a cyclic polyethyleneoxide having six ethyleneoxide units), quarternary ammonium salts and the like. It is believed that the solid-liquid system requires the use of a polar solvent agent to cause the reaction to proceed. It is further generally accepted that the reaction can be caused to proceed more rapidly by the presence of a phase transfer agent because the phase transfer agent forms stable complexes with the alkali metal cation and is able to solubilize the inorganic salt in moderately polar solvents to provide "naked anions" which are highly reactive in the nucleophilic substitution reaction (Angew. Chem. Int. Ed. Eng. 17 (1978) No. 1, Pg. 62). Such systems have not been widely used because they require purification of the nitroparaffin from the aprotic solvent and the separation and recovery of the expensive catalytic materials.

Early work as taught in U.S. Pat. Nos. 2,105,581 and 2,117,931, was done to manufacture nitroalkanes using a liquid/gas phase system in which a $C_1$-$C_6$ alkyl halide gas was passed through aqueous sodium nitrite solutions of about 1 to 10 mols. Although the corresponding nitroalkane was formed, the rate of reaction was very low and, therefore, the process did not achieve commercial importance.

It is desired to form nitroalkane, in particular nitromethane, by a simple process which does not require the arduous separation and recovery of catalytic amounts of material, which does not require the use of expensive materials to enhance the reaction rate and, most importantly, produces the desired product in good yields and at a substantial reaction rate to provide a commercially attractive process.

SUMMARY OF THE INVENTION

A process for forming nitromethane by contacting methyl halide with an alkali or alkaline earth metal nitrite in the presence of excess methyl halide.

DETAILED DESCRIPTION OF THE INVENTION

The present invention is directed to a simple economical method of forming nitromethane by reacting a methyl halide with an alkali or alkaline earth metal nitrite in the presence of excess of the methyl halide.

The methyl halide reagent can be methyl chloride, methyl bromide or methyl iodide. It is preferred that the reagent be methyl chloride due to its low cost, availability and its ability to form the desired nitromethane in good yields and at good reaction rates. The ability to utilize readily available and inexpensive methyl chloride both as a reactive reagent and as a solvent aids in providing a commercially desirable, cost effective process.

The nitrite reagent can be any alkali or alkaline earth metal nitrite such as sodium nitrite, potassium nitrite or calcium nitrite. The most preferred nitrite is sodium nitrite because it enhances the reaction rate, is readily available and inexpensive.

The reaction is carried out by contacting the alkali or alkaline earth metal nitrite with the methyl halide in the presence of a sufficient excess of the methyl halide to act as the reaction medium. For purposes of simplicity the reaction zone should contain only one methyl halide as both the reactant and the reaction medium. The amount of excess of methyl halide should be such that the molar ratio of metal nitrite to methyl halide is from about 1:2 to 1:100 with ratios of from 1:3 to 1:20 being preferred. It is critical that the methyl halide be present in excess of that required for a stoichiometric ratio and in sufficient amount to permit it to act as carrier and reacton medium.

The reaction zone can contain additional materials which are at least partially miscible with the methyl halide. These materials must be present in minor amounts by weight based on the amount of methyl halide present. The combined amount of additional materials (the term "additional materials" shall mean herein and in the claims any material which is at least partially miscible in the methyl halide) should not exceed 40 percent by weight based on the weight of all of the additional material(s) and the excess amount (over stoichiometric amount required to react with nitrite) of methyl halide present in the reaction zone and preferably less than 30 percent. These additional materials can include conventional polar solvent liquids such as organic polar solvents as, for example, methanol, dimethyl formamide, dimethyl sulfoxide, N-methyl pyrrolidone, acetone and the like or water and/or conventional phase transfer agents, such as for example, crown ethers as 18-crown-6, 15-crown-5 and the like, quaternary ammonium salts, such as for example, tetra ($C_1$-$C_8$) alkyl ammonium halides, and the like or nonpolar liquids such as benzene, toluene and the like.

Previously described processes to form nitromethane from methyl halide and a nitrite salt have been taught to be required to be carried out in large excess amounts of polar solvents in comparison to the methyl halide present. It has presently been found that the desired results of high reaction rate and yield of nitromethane is unexpectedly achieved by using methyl halide as the sole or major component of the reaction zone medium. Presence of large amounts of certain aprotic solvents, such as water, methanol and the like, have been found to have detrimental effect on the yield/rate properties in comparison to that presently achieved. In addition, certain aprotic solvents, though tolerable in larger amounts cause recovery and economic problems. The presence of large amounts of such solvents should be avoided.

It has been further unexpectedly found that when the present process is carried out with the required excess of methyl halide and in the presence of a small amount of ater as the sole or major additional material one achieves superior rates of reaction and conversion to the desired nitromethane. However, as stated above with respect to the polar solvents generally, larger amounts of water have been found to have detrimental effects on the present process. The presence of small quantities of water not only has been found to further enhance the process but also has the advantages being inexpensive, readily available and easily separated from the methyl halide and nitromethane due to its very low solubility with such materials.

In addition, a buffering agent which is capable of maintaining the system at a pH of from about 5 to about 10, and preferably between about 6 to 9.5 can be present in the reaction zone. Useful agents include sodium bicarbonate, calcium carbonate, sodium acetate and the like. Such buffering agents can be present in up to about 100 weight percent based on the nitrite salt present in the reaction zone. Excess buffering agent may be present but is not believed to add to the results attained.

The total amount of the various additive materials which are at least partially miscible in the methyl halide, i.e. conventional catalyst, polar solvent, and nonpolar inert liquids, may be present in the reaction zone in amounts not to exceed about 40 weight percent based on the combined weight of the additive materials and the excess (over stoichiometric amount required to react with the metal nitrite present) of methyl halide.

The reaction is carried out by contacting the methyl halide with the metal nitrite salt in the presence of excess methyl halide. The reaction can be run at temperatures of from about ambient to about 120° C. in a closed vessel. The reaction should be carried out under conditions which cause at least the majority of the methyl halide to remain in a liquid state. This can be readily done by performing the reaction under pressure. The pressure can be the autogenous pressure formed by the materials in the reaction zone at the reaction temperature or the pressure can be induced by introduction of an inert gas such as argon, nitrogen or the like to the reaction zone. The time of contact can be from about 10 minutes to about 12 hours with from about 30 minutes to 6 hours being more preferred and from 3 to 6 hours being most preferred. The nitromethane product can be recovered by separating it, through distillation or the like means. The excess methyl halide alone or in combination with any other of the added components can be recycled to the reaction zone. For example, the process can be carried out by charging a vessel capable of being sealed with a metal nitrite, such as sodium nitrite, a buffering agent, such as sodium bicarbonate, and with a small amount of water. Liquid methyl chloride is then transferred to the vessel in sufficient quantity. The vessel is sealed, heated, and rocked to agitate the contents for a prescribed period of time, such as three to four hours. The reaction vessel is cooled and the materials separated by distillation with the methyl chloride being removed first and returned for use in a subsequent run. The water and nitromethane azeotropically distill off and can be further separated and then pure nitromethane is removed by distillation (B.P. 101° C.). Other conventional means can be used as can be readily determined by those skilled in the art.

The following examples are given for illustrative purposes only and are not deemed to be a limitation on the inventions except as defined by the claims appended hereto. All parts and percentages are by weight unless otherwise stated.

EXAMPLE I

A stainless steel reaction vessel of 10 cc volume was charged with 0.56 part sodium nitrite, 0.8 part of distilled water and 0.34 part sodium bicarbonate. The vessel was cooled with liquid nitrogen under a blanket of argon to assure lack of air moisture condensation in the vessel. To the chilled vessel was added 3.9 parts of liquid methyl chloride (measured and weighed at $-77°$ C. with density taken at 1.1). 3.5 parts of the added methyl chloride was excess over that required for stoichiometry. The vessel was sealed and heated at 75° C. for 4 hours with agitation. The resultant material was analyzed by conventional gas chromatographic analysis and showed that nitromethane was obtained in 57 percent yield. The selectivity to nitromethane was 74 percent based on the sodium nitrite.

EXAMPLE II

Example I above was repeated except that the sodium bicarbonate additive was not present. The reaction produced a 45 percent yield of nitromethane as analyzed by gas chromatography. The selectivity to nitromethane was 56 percent based on sodium nitrite.

EXAMPLE III

For comparative purposes, Example II was repeated except that the methyl chloride was used in stoichiometric amounts with respect to the sodium nitrite, i.e. 0.4 part methyl chloride. The reaction was thereby carried out in the presence of excess water at a 10 molar solution of sodium nitrite as described in U.S. Pat. No. 2,105,581. The resultant material was analyzed by gas chromatography and showed that nitromethane was formed in very low yield of <1 percent.

This example illustrates that the absence of excess methyl chloride severely retards the rate of formation and thereby the yield (on a back to back basis with the present process) of nitromethane.

EXAMPLE IV

The process of Example I was repeated except that the amount of methyl chloride was reduced to 3.3 parts (thereby having 2.9 parts excess present), 0.4 part distilled water was used and 0.05 part of 18-crown-6, a cyclic ethylene oxide of 6 units, was present. The reaction was carried out for 5.5 hours at 65° C. Gas chromatography analysis showed a 47 percent yield of nitromethane.

EXAMPLE V

The process of Example IV was repeated except that the water was replaced with 0.3 part methanol and the reaction was run for 7 hours. The G.C. analysis showed a 59 percent yield of the desired nitromethane.

EXAMPLE VI

The process of Example IV was repeated except that no water or other solvent was used and the crown ether was replaced by an equal amount of hexadecyltrimethyl ammonium bromide. The nitromethane was formed in 40 percent yield as analyzed by gas chromotography.

While the invention has been described in connection with certain preferred embodiments, it is not intended to limit the invention to the particular form set forth, but, on the contrary it is intended to cover such alternatives, modifications and equivalents as defined by the appended claims.

What is claimed is:

1. A process for forming nitromethane comprising contacting in a reaction zone an alkali metal or alkaline earth metal nitrite with a methyl halide under elevated pressure and at a temperature and a time sufficient to produce nitromethane, the ratio of methyl halide to metal nitrite being at least about 2:1 and separating and recovering the formed nitromethane.

2. The process of claim 1 wherein the reaction zone further contains a polar liquid in an amount of up to 40 percent by weight based on the combined weight of polar liquid and excess methyl halide contained in the reaction zone.

3. The process of claim 1 wherein the reaction zone further contains a phase transfer agent in an amount of up to 40 percent by weight based on the combined weight of phase transfer agent and excess methyl halide contained in the reaction zone.

4. The process of claim 1 wherein the reaction zone contains an agent capable of and in an amount sufficient to maintain a pH of between 5 and 10.

5. The process of claim 1 wherein the reaction zone further contains a polar liquid and a phase transfer agent, said liquid and said agent present in a combined amount of up to 40 percent by weight based on the combined weight of said liquid, agent and excess methyl halide contained in the reaction zone.

6. The process of claim 2 or 5 wherein the polar liquid is water.

7. The process of claim 1, 2, 3, 4, or 5 wherein the reaction is carried out under autogenous pressure and at a temperature of from about 40° to about 120° C.

* * * * *